United States Patent [19]
Zambounis et al.

[11] Patent Number: 5,616,725
[45] Date of Patent: Apr. 1, 1997

[54] PYRROLO[3,4-C]PYRROLE SYNTHESIS

[75] Inventors: John S. Zambounis, Murten; Zhimin Hao, Marly; Abul Iqbal, Arconciel, all of Switzerland

[73] Assignee: Ciba-Geigy Corporation, Tarrytown, N.Y.

[21] Appl. No.: 541,004

[22] Filed: Oct. 11, 1995

Related U.S. Application Data

[62] Division of Ser. No. 319,406, Oct. 6, 1994, Pat. No. 5,484,943.

[30] Foreign Application Priority Data

| Oct. 13, 1993 | [CH] | Switzerland | 3079/93 |
| Jun. 29, 1994 | [CH] | Switzerland | 2074/94 |
| Jun. 29, 1994 | [CH] | Switzerland | 2075/94 |
| Jun. 29, 1994 | [CH] | Switzerland | 2076/94 |

[51] Int. Cl.$^6$ .................................. C07D 487/04
[52] U.S. Cl. ................ 548/453; 548/215; 548/217; 548/312.1; 548/159; 546/256; 546/276.7; 544/284; 544/111; 544/373; 546/275.4; 546/271.4; 546/271.7; 546/270.1; 546/272.4; 546/273.4; 546/272.7; 546/268.4; 546/14; 546/187; 546/193; 546/194
[58] Field of Search .................. 548/453; 546/272; 544/111, 284, 373

[56] References Cited

U.S. PATENT DOCUMENTS

| 4,585,878 | 4/1986 | Jost et al. ............... 548/453 |
| 4,791,204 | 12/1988 | Jost et al. ............... 548/101 |
| 4,826,976 | 5/1989 | Borror et al. ............ 544/58.4 |
| 5,243,052 | 9/1993 | Taylor et al. ............ 546/154 |

FOREIGN PATENT DOCUMENTS

| 0133156 | 2/1985 | European Pat. Off. . |
| 0224445 | 6/1987 | European Pat. Off. . |
| 0353184 | 1/1990 | European Pat. Off. . |
| 0499011 | 8/1992 | European Pat. Off. . |
| 4123175 | 4/1992 | Japan . |

OTHER PUBLICATIONS

Iqbal et al., Derwent abstract 90-031710[os] For EP353,184A (1990).

*Primary Examiner*—David B. Springer
*Attorney, Agent, or Firm*—Michele A. Kovaleski; George R. Dohmann

[57] ABSTRACT

Pyrrolo[3,4-c]pyrroles of formula (I)

wherein
D and E are each independently of the other a group of formula $$-CO{-}(X)_m{-}(Y)_n{-}(CO)_p{-}\text{Ar}(R_8)(R_9) \quad (II)$$

$$-CO{-}(X)_m{-}(Z)_n{-}Q \quad (III)$$

or $$-CO-N(R_{10})(R_{11}) \quad (IV)$$

The symbols Q, $R_8$, $R_9$, $R_{10}$, $R_{11}$, X, Y, Z, m and n are as defined in claim 1.

These pyrrolo[3,4-c]pyrroles are distinguished by outstanding solid state fluorescence in the UV range as well as by the ease with which they can be converted to pyrrolopyrrole pigments even in the substrate in which they are incorporated.

7 Claims, No Drawings

PYRROLO[3,4-C]PYRROLE SYNTHESIS

This is a division of Ser. No. 08/319,406, filed Oct. 6, 1994 U.S. Pat. No. 5,484,943.

The present invention relates to novel pyrrolo[3,4-c] pyrroles containing carbamate groups, to their preparation and to the use therefore as fluorescent pigments as well as pigment precursors which can be readily converted into the corresponding diketopyrrolopyrrole pigments.

N-substituted pyrrolo[3,4-c]pyrroles are disclosed in U.S. Pat. Nos. 4,585,878 and 4,791,204. From the generic definition of all substituents it can be inferred that the N-substituents may also be, inter alia, alkoxycarbonyl groups, which are defined in U.S. Pat. No. 4,791,204 as including methoxycarbonyl, ethoxycarbonyl, n-propoxycarbonyl, n-butoxycarbonyl and n-hexyloxycarbonyl. Specific pyrrolo[3,4-c]pyrroles containing carbamate groups are not disclosed. U.S. Pat. No. 4,585,878 teaches that the N-substituted pyrrolo[3,4-c]pyrroles disclosed therein exhibit high fluorescence in dissolved form in polymers.

The invention provides novel carbamate group-containing pyrrolo[3,4-c]pyrroles which, surprisingly, exhibit a very high solid state fluorescence, especially in the UV range, and which are readily convertible into the corresponding diketopyrrolopyrrole pigments with simultaneous displacement of the absorption spectrum, and hence open the way to unexpected applications.

Accordingly, the invention relates to pyrrolo[3,4-c]pyrroles of formula

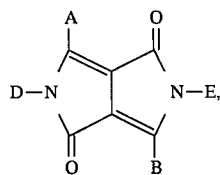

(I)

wherein

A and B are each independently of the other a group of formula

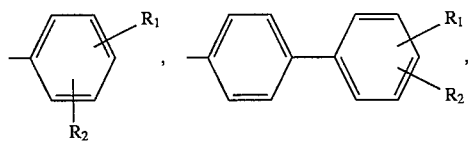

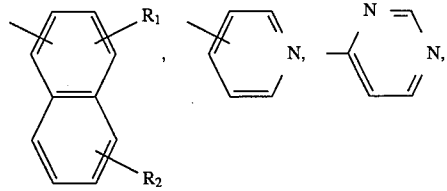

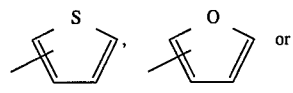

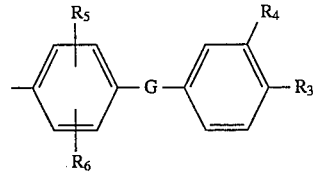

wherein $R_1$ and $R_2$ are each independently of the other hydrogen, halogen, $C_1$–$C_{18}$alkyl, $C_1$–$C_{18}$alkoxy, $C_1$–$C_{18}$alkylmercapto, $C_1$–$C_{18}$alkylamino, —CN, —NO$_2$, -phenyl, trifluoromethyl, $C_5$–$C_6$cycloalkyl, —C=N—($C_1$–$C_{18}$alkyl),

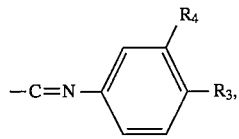

imidazolyl, pyrrazolyl, triazolyl, piperazinyl, pyrrolyl, oxazolyl, benzoxazolyl, benzothiazolyl, benzimidazolyl, morpholinyl, piperidinyl or pyrrolidinyl, G is —CH$_2$—, —CH(CH$_3$)—, —C(CH$_3$)$_2$—, —CH=N—, —N=N—, —O—, —S—, —SO—, —SO$_2$— or —NR$_7$—, $R_3$ and $R_4$ are each independently of the other hydrogen, halogen, $C_1$–$C_6$alkyl, $C_1$–$C_{18}$alkoxy or —CN, $R_5$ and $R_6$ are each independently of the other hydrogen, halogen or $C_1$–$C_6$alkyl and $R_7$ is hydrogen or $C_1$–$C_6$alkyl, D and E are each independently of the other a group of formula

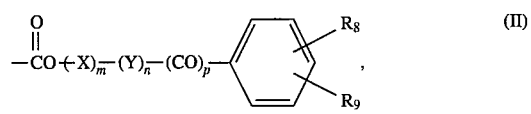 (II)

 (III)

or

 (IV)

and D may also be hydrogen, and in formulae II, III and IV m, n and p are each independently of one another 0 or 1, X is $C_1$–$C_{14}$alkylene or $C_2$–$C_8$alkenylene, Y is a group —V—(CH$_2$)$_q$—, Z is a group —V—(CH$_2$)$_r$—, V is $C_3$–$C_6$cycloalkylene, q is an integer from 1 to 6, and r is an integer from 0 to 6, $R_8$ and $R_9$ are each independently of the other hydrogen, $C_1$–$C_6$alkyl, $C_1$–$C_4$alkoxy, halogen, CN, NO$_2$, unsubstituted phenyl or phenoxy or phenyl or phenoxy which are substituted by $C_1$–$C_4$alkyl, $C_1$–$C_4$alkoxy or halogen, Q is hydrogen, CN, Si(R$_8$)$_3$, a group C(R$_{12}$)(R$_{13}$)(R$_{14}$), wherein R$_{12}$, R$_{13}$ and R$_{14}$ are halogen, a group

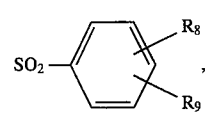

wherein R$_8$ and R$_9$ are as defined above, a group SO$_2$R$_{15}$ or SR$_{15}$, wherein R$_{15}$ is $C_1$–$C_4$alkyl, a group CH(R$_{16}$)$_2$, wherein R$_{16}$ is unsubstituted phenyl or phenyl which is substituted by C$_1$–C$_4$alkyl, C$_1$–C$_4$alkoxy or halogen, or a group of formula

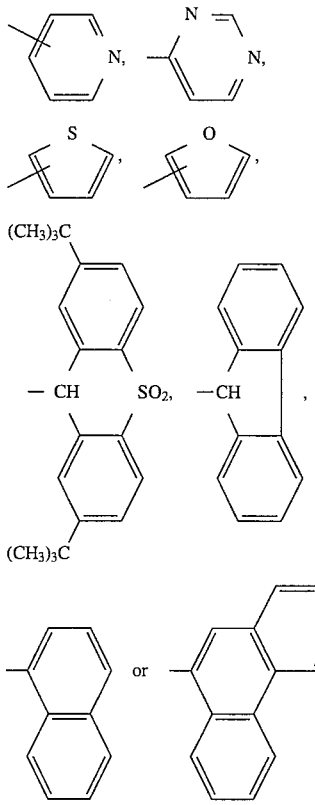

R$_{10}$ and R$_{11}$ are each independently of the other hydrogen, C$_1$–C$_{18}$alkyl a group

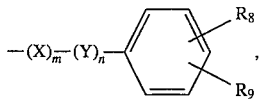

wherein X, Y, R$_8$, R$_9$, m and n are as defined above, or R$_{10}$ and R$_{11}$, together with the linking nitrogen atom, form a pyrrolidinyl, piperidinyl or morpholinyl radical, with the proviso that, if D and/or E are a group of formula III, Q is hydrogen and n is 0, m must be 1 and X a C$_2$–C$_{14}$alkylene or C$_2$–C$_8$alkenylene group which is branched at the carbon atom attached to the oxygen atom.

X in the significance of C$_1$–C$_{14}$alkylene is straight-chain or branched alkylene, typically methylene, dimethylene, trimethylene, 1-methylmethylene, 1,1-dimethylmethylene, 1,1-dimethyldimethylene, 1,1-dimethyltrimethylene, 1-ethyldimethylene, 1-ethyl-1-methyldimethylene, tetramethylene, 1,1-dimethyltetramethylene, 2,2-dimethyltrimethylene, hexamethylene, decamethylene, 1,1-dimethyldecamethylene, 1,1-diethyldecamethylene or tetradecamethylene.

X in the significance of C$_2$–C$_8$alkenylene is straight-chain or branched alkenylene, typically vinylene, allylene, methallylene, 1-methyl-2-butenylene, 1,1-dimethyl-3-butenylene, 2-butenylene, 2-hexenylene, 3-hexenylene or 2-octenylene.

Halogen substituents may be iodo, fluoro, preferably bromo and, most preferably, chloro.

C$_1$–C$_6$Alkyl will typically be methyl, ethyl, n-propyl, isopropyl, n-butyl, sec-butyl, tert-butyl, n-amyl, tert-amyl, hexyl, and C$_1$–C$_{18}$alkyl may additionally be heptyl, octyl, 2-ethylhexyl, nonyl, decyl, dodecyl, tetradecyl, hexadecyl or octadecyl.

C$_1$–C$_4$Alkoxy is typically methoxy, ethoxy, n-propoxy, isopropoxy, butoxy, and C$_1$–C$_{18}$alkoxy may additionally be hexoxy, decyloxy, dodecyloxy, hexadecyloxy or octadecyloxy.

C$_1$–C$_{18}$Alkylmercapto is typically methylmercapto, ethylmercapto, propylmercapto, butylmercapto, octylmercapto, decylmercapto, hexadecylmercapto or octadecylmercapto.

C$_1$–C$_{18}$Alkylamino is typically methylamino, ethylamino, propylamino, hexylamino, decylamino, hexadecylamino or octadecylamino.

C$_5$–C$_6$Cycloalkyl is typically cyclopentyl and, preferably, cyclohexyl.

C$_3$–C$_6$Cycloalkylene is typically cyclopropylene, cyclopentylene and, preferably, cyclohexylene.

Particularly interesting pyrrolo[3,4-c]pyrroles of formula I are those wherein A and B are each independently of the other a group of formula

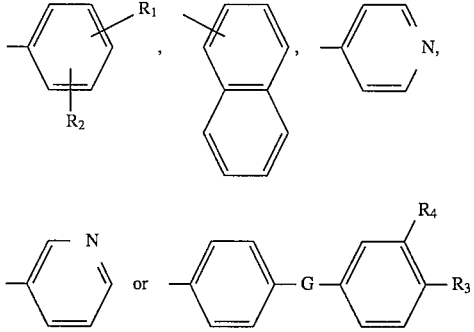

wherein

R$_1$ and R$_2$ are each independently of the other hydrogen, chloro, bromo, C$_1$–C$_4$alkyl, C$_1$–C$_6$alkoxy, C$_1$–C$_6$alkylamino, CN or phenyl, G —O—, —NR$_7$—, —N=N— or —SO$_2$—, R$_3$ and R$_4$ are hydrogen and R$_7$ is hydrogen, methyl or ethyl, and A and B are preferably both identical; and, more particularly, those wherein A and B are a group of formula

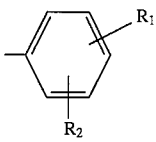

wherein

R$_1$ and R$_2$ are each independently of the other hydrogen, methyl, tert-butyl, chloro, bromo, CN or phenyl. R$_2$ is preferably hydrogen.

Preferred pyrrolo[3,4-c]pyrroles of formula I are those wherein D is hydrogen or has the meaning of E and E is a group of formula

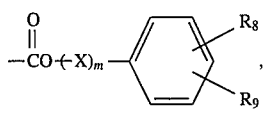

(V)

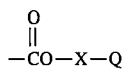

or (IV)

wherein m is 0 or 1,

X is $C_1$-$C_4$alkylene or $C_2$-$C_5$alkenylene, $R_8$ and $R_9$ are each independently of the other hydrogen, $C_1$-$C_4$alkyl, methoxy, chloro or —$NO_2$—, and Q is hydrogen, CN, $CCl_3$, a group

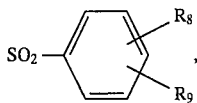

$SO_2CH_3$ or $SCH_3$, $R_{10}$ and $R_{11}$ are each independently of the other hydrogen, $C_1$-$C_4$alkyl or a group

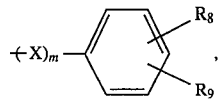

or $R_{10}$ and $R_{11}$, taken together, form a piperidinyl radical, with the proviso that, if D and/or E is a group of formula IX and Q is hydrogen, X must be a group

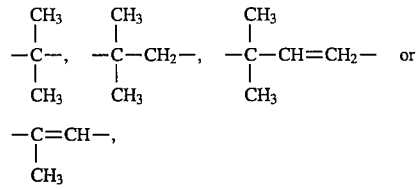

especially if D and E are identical and are a group of formula

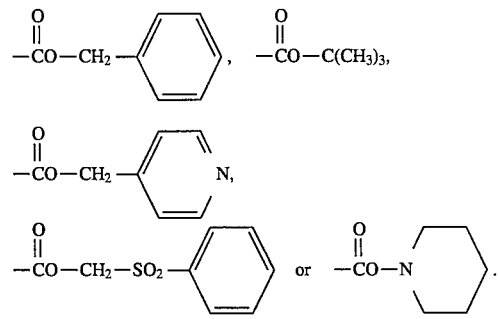

The meaning here is that preferred radicals D and E can also be combined with preferred radicals A and B.

In U.S. Pat. No. 4,585,878 it is said in connection with the preparation of N-substituted pyrrolpyrroles that they can be obtained by reacting a N-substituted pyrrolo-3,4-c-pyrrole with a compound that carries the corresponding N-substituents as leaving groups in an organic solvent. In the sole Example describing a compound containing a N-carbonyl group (Example 9: N-benzoyl), 1,4-diketo-3,6-diphenyl-pyrrolo[3,4-c]pyrrole is reacted with benzoyl chloride. In the experiment to prepare the desired carbamates in analogous manner by reaction with a corresponding acid chloride derivative, it was unfortunately found that it was only possible to obtain said carbamates in poor yield.

Very surprisingly, however, it was observed that when using appropriate trihaloacetates, azides, carbonates, alkylidene-iminooxyformates or, in particular, appropriate dicarbonates, the desired carbamates are obtained in very good yield. An improved yield is also obtained—even if only to a lesser degree—by carrying out the reaction with an aliphatic acid chloride derivative, conveniently butyl chloroformate, in the presence of a base as catalyst.

Accordingly, the invention further relates to a process for the preparation of pyrrolo[3,4-c]pyrroles of formula

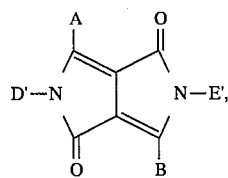

(VII)

wherein

A and B are each independently of the other a group of formula

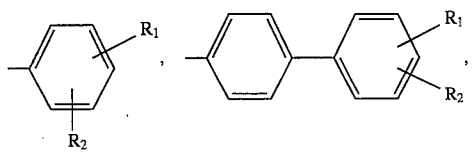

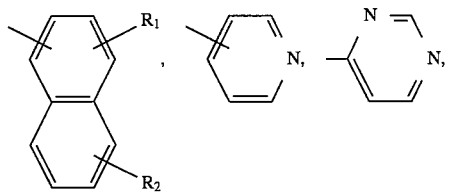

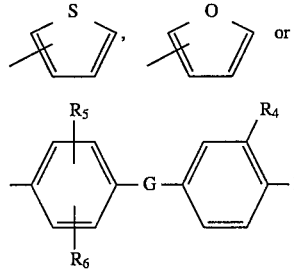

wherein $R_1$ and $R_2$ are each independently of the other hydrogen, halogen, $C_1$-$C_{18}$alkyl, $C_1$-$C_{18}$alkoxy, $C_1$-$C_{18}$alkylmercapto, $C_1$-$C_{18}$alkylamino, —CN, —$NO_2$, -phenyl, trifluoromethyl, $C_5$-$C_6$cycloalkyl, —C=N—($C_1$-$C_{18}$alkyl),

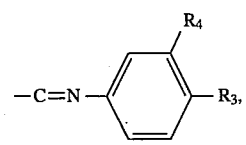

imidazolyl, pyrrazolyl, triazolyl, piperazinyl, pyrrolyl, oxazolyl, benzoxazolyl, benzothiazolyl, benzimidazolyl, morpholinyl, piperidinyl or pyrrolidinyl, G is —CH$_2$—, —CH(CH$_3$)—, —C(CH$_3$)$_2$—, —CH=N—, —N=N—, —O—, —S—, —SO—, —SO$_2$— or —NR$_7$—, R$_3$ and R$_4$ are each independently of the other hydrogen, halogen, C$_1$-C$_6$alkyl, C$_1$-C$_{18}$alkoxy or —CN, R$_5$ and R$_6$ are each independently of the other hydrogen, halogen or C$_1$-C$_6$alkyl and R$_7$ is hydrogen or C$_1$-C$_6$alkyl, D' and E' are each independently of the other a group of formula

    (II)

    (III)

or

    (IV)

and D' may also be hydrogen, and in formulae II, III and IV m, n and p are each independently of one another 0 or 1, X is C$_1$-C$_{14}$alkylene or C$_2$-C$_8$alkenylene, Y is a group —V—(CH$_2$)$_q$—, Z is a group —V—(CH$_2$)$_r$—, V is C$_3$-C$_6$cycloalkylene, q is an integer from 1 to 6, and r is an integer from 0 to 6, R$_8$ and R$_9$ are each independently of the other hydrogen, C$_1$-C$_6$alkyl, C$_1$-C$_4$alkoxy, halogen, CN, NO$_2$, unsubstituted phenyl or phenoxy or phenyl or phenoxy which are substituted by C$_1$-C$_4$alkyl, C$_1$-C$_4$alkoxy or halogen, Q is hydrogen, CN, Si(R$_8$)$_3$, is a group C(R$_{12}$)(R$_{13}$)(R$_{14}$), wherein R$_{12}$, R$_{13}$ and R$_{14}$ are halogen, a group

wherein R$_8$ and R$_9$ are as defined above, a group SO$_2$R$_{15}$ or SR$_{15}$, wherein R$_{15}$ is C$_1$-C$_4$alkyl, a group CH(R$_{16}$)$_2$, wherein R$_{16}$ is unsubstituted phenyl or phenyl which is substituted by C$_1$-C$_4$alkyl, C$_1$-C$_4$alkoxy or halogen, or a group of formula

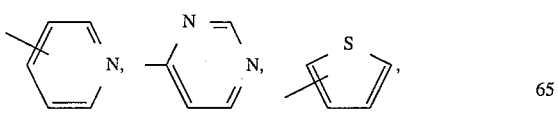

-continued

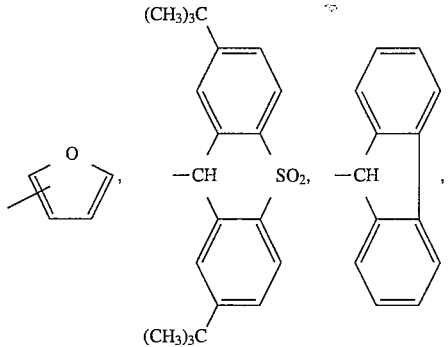

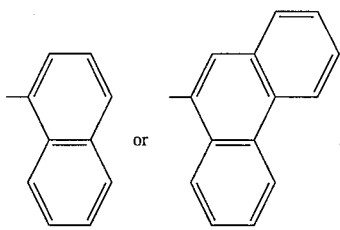

R$_{10}$ and R$_{11}$ are each independently of the other hydrogen, C$_1$-C$_{18}$alkyl a group

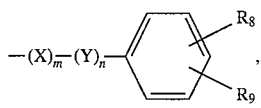

wherein X, Y, R$_8$, R$_9$, m and n are as defined above, or R$_{10}$ and R$_{11}$, together with the linking nitrogen atom, form a pyrrolidinyl, piperidinyl or morpholinyl radical, which process comprises reacting a pyrrolo[3,4-c]pyrrole of formula

    (VIII)

wherein A and B are as defined above, in the desired molar ratio with a dicarbonate of formula

E'-O-E'    (IX)

or with a trihaloacetate of formula (R$_{17}$)$_3$C-E'    (X)

or with a 1:1 mixture of a dicarbonate of formula IX and a dicarbonate of formula

D'-O-D'    (XI)

or with a 1:1 mixture of a trihaloacetate of formula X and a trihaloacetate of formula (R$_{17}$)$_3$C-D'    (XII), or with an azide of formula

    (XIII), which may also be used in a 1:1 mixture with

    (XIV)

or with a carbonate of formula

    (XV), which may also be used in a 1:1 mixture with

    (XVI)

or with an alkylidene-iminooxyformate of formula

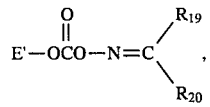    (XVII)

which can also be used in a 1:1 mixture with

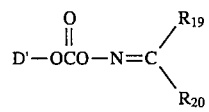    (XVIII)

wherein D' and E' are each as defined above, $R_{17}$ is chloro, fluoro or bromo, $R_{18}$ is $C_1$–$C_4$alkyl or unsubstituted phenyl or phenyl which is substituted by halogen, $C_1$–$C_4$alkyl, $C_1$–$C_4$alkoxy or —CN, $R_{19}$ is —CN or —COOR$_{18}$, and $R_{20}$ is unsubstituted phenyl or phenyl which is substituted by halogen, $C_1$–$C_4$alkyl, $C_1$–$C_4$alkoxy or —CN, in an aprotic organic solvent and in the presence of a base as catalyst, conveniently in the temperature range from 0° to 400° C., preferably from 10° to 200° C., for 2 to 80 hours.

It is preferred to react the pyrrolo[3,4-c]pyrrole of formula VIII with a dicarbonate of formula IX or with a 1:1 mixture of dicarbonate of formula IX and dicarbonate of formula XI.

Pyrrolo[3,4-c]pyrroles of formula VIII, dicarbonates of formulae IX and XI, trihaloacetates of formulae X and XII, azides of formulae XIII and XIV, carbonates of formulae XV and XVI, and alkylidene-iminooxyformates of formulae XVII and XVIII, are known substances. Any that are novel can be prepared by methods analogous to standard known ones.

The respective molar ratio of pyrrolo[3,4-c]pyrrole to the compounds of formulae IX–XVIII will depend on the radicals D and E to be introduced. Preferably, however, the compounds of formulae IX–XVIII will be used in a 2- to 10-fold excess.

Suitable solvents are typically ethers such as tetrahydrofuran or dioxane, or glycol ethers such as ethylene glycol methyl ether, ethylene glycol ethyl ether, diethylene glycol monomethyl ether or diethylene glycol monoethyl ether, and also dipolar aprotic solvents such as acetonitrile, benzonitrile, N,N-dimethylformamide, N,N-dimethylacetamide, nitrobenzene, N-methylpyrrolidone, halogenated aliphatic or aromatic hydrocarbons such as trichloroethane, benzene or alkyl-, alkoxy- or halogen-substituted benzene, typically including toluene, xylene, anisole or chlorobenzene, or aromatic N-heterocycles such as pyridine, picoline or quinoline. Preferred solvents are typically tetrahydrofuran, N,N-dimethylformamide and N-methylpyrrolidone. The cited solvents may also be used as mixtures. It is convenient to use 5–20 parts by weight of solvent to 1 part by weight of reactant.

Bases suitable as catalysts are typically the alkali metals themselves, conveniently lithium, sodium or potassium and the hydroxides or carbonates thereof, or alkali metal amides such as lithium, sodium or potassium amide or alkali metal hydrides such as lithium, sodium or potassium hydride, or alkaline earth metal or alkali metal alcoholates which are derived in particular from primary, secondary or tertiary aliphatic alcohols of 1 to 10 carbon atoms, for example lithium, sodium or potasssium methylate, ethylate, n-propylate, isopropylate, n-butylate, sec-butylate, tert-butylate, 2-methyl-2-butylate, 2-methyl-2-pentylate, 3-methyl-3-pentylate, 3-ethyl-3-pentylate, and also organic aliphatic aromatic or heterocyclic N-bases, typically including diazabicyclooctene, diazabicycloundecene and 4-dimethylaminopyridine and trialkylamines such as trimethylamine or triethylamine. A mixture of the cited bases may also be used.

The organic nitrogen bases are preferred, for example diazabicyclooctene, diazabicycloundecene and preferably, 4-dimethylaminopyridine.

The reaction is preferably carried out in the temperature range from 10° to 100° C., most preferably from 14° to 40° C., and under atmospheric pressure.

The novel pyrrolopyrroles are admirably suitable for use as fluorescent pigments for the mass colouration of organic material of high molecular weight.

Illustrative examples of high molecular weight organic materials which can be coloured with the novel compounds of formula I are vinyl polymers such as polystyrene, poly-α-methylstyrene, poly-p-methylstyrene, poly-p-hydroxystyrene, poly-p-hydroxyphenylstyrene, poly(methylacrylate) and poly(acrylamide) as well as the corresponding methacrylic compounds, poly(methylmaleate), poly(acrylonitrile), poly(methacrylonitrile), poly(vinyl chloride), poly(vinyl fluoride), poly(vinylidene chloride), poly(vinylidene fluoride), poly(vinyl acetate), poly(methyl vinyl ether) and poly(butyl vinyl ether); novolaks derived from $C_1$–$C_6$aldehydes, typically formaldehyde and acetaldehyde, and a binuclear, preferably mononuclear, phenol which may be substituted by one or two $C_1$–$C_9$alkyl groups, one or two halogen atoms or a phenyl ring, for example o-, m- or p-cresol, xylene, p-tert-butyl phenol, o-, m- or p-nonylphenol, p-chlorophenol or p-phenylphenol, or from a compound containing more than one phenolic group, e.g. resorcinol, bis(4-hydroxyphenyl)methane or 2,2-bis(4-hydroxyphenyl)propane; polymers derived from maleimide and/or maleic anhydride, e.g. copolymers of maleic anhydride and styrene; poly(vinylpyrrolidone), biopolymers and derivatives thereof such as cellulose, starch, chitine, chitosane, gelatin, zein, ethyl cellulose, nitrocellulose, cellulose acetate and cellulose butyrate; natural resins and synthetic resins such as rubber, casein, silicone and silicone resins, ABS, urea/formaldehyde and melamine/formaldehyde resins, alkyd resins, phenolic resins, polyamides, polyimides, polyamide/imides, polysulfones, polyether sulfones, polyphenylene oxides, polyurethanes, polyureas, polycarbonates, polyarylenes, polyarylenesulfides, polyepoxides, polyolefins and polyalkadienes. Preferred high molecular weight organic materials are typically cellulose ethers and esters, for example ethyl cellulose, nitrocellulose, cellulose acetate or cellulose butyrate, natural resins or synthetic resins such as polymerisation or condensation resins, for example aminoplasts, in particular urea/formaldehyde and melamine/formaldehyde resins, alkyd resins, phenolic plastics, polycarbonates, polyolefins, polystyrene, polyvinyl chloride, polyamides, polyurethanes, polyesters, ABS, polyphenylene oxide, rubber, casein, silicone and silicone resins, singly or in mixtures.

The above high molecular weight organic compounds may be singly or as mixtures in the form of plastic materials, melts or of spinning solutions, paint systems, coating materials or printing inks. Depending on the end use requirement, it is expedient to use the novel pigment salts as toners or in the form of preparations.

The novel pyrrolopyrroles are particularly suitable for the mass coloration of polyesters, polyvinyl chloride and, preferably, polyolefins such as polyethylene and polypropylene and ABS as well as paint systems, also powder coating compositions, printing inks and coating materials.

The novel pyrrolopyrroles can be used in an amount of 0.01 to 30% by weight, preferably 0.1 to 10% by weight, based on the high molecular weight organic material to be pigmented.

The pigmenting of the high molecular weight organic materials with the pyrrolopyrroles of this invention is conveniently effected by incorporating a pyrrolopyrrole by itself or in the form of a masterbatch in the substrates using roll mills, mixing or milling apparatus. The pigmented material is then brought into the desired final form by methods which are known per se, conveniently by calendering, moulding, extruding, coating, casting or by injection moulding. It is often desirable to incorporate plasticisers into the high molecular weight compounds before processing in order to produce non-brittle mouldings or to diminish their brittleness. Suitable plasticisers are typically esters of phosphoric acid, phthalic acid or sebacic acid. The plasticisers may be incorporated before or after blending the pigment salts of this invention into the polymers. To obtain different shades it is also possible to add fillers or other chromophoric components such as white, coloured or black pigments in any amount to the high molecular weight organic materials in addition to the pyrrolopyrroles of this invention.

For pigmenting paint systems, coating materials and printing inks, the high molecular weight organic materials and the pyrrolopyrroles of this invention, together with optional additives such as fillers, other pigments, siccatives or plasticisers, are finely dispersed or dissolved in a common organic solvent or mixture of solvents. The procedure may be such that the individual components by themselves, or also several components together, are dispersed or dissolved in the solvent and thereafter all the components are mixed.

When used for colouring, inter alia, polyvinyl chloride or polyolefins, the pyrrolopyrroles of this invention have good allround pigment properties, including good fastness to migration, light and weathering, and especially unexpectedly high fluorescence.

Of very great importance, however, is the entirely unexpected ease with which the pyrrolopyrroles of this invention—even in the substrate in which they have already been incorporated—can be converted to the corresponding pyrrolopyrrole pigments of formula VIII. This can be done in the simplest manner, whether by thermal treatment (heating to the temperature range from 50° to 400° C., preferably from 100° to 200° C. or laser radiation), photolytic treatment (exposure to wavelengths below e.g. 375 nm) or chemical treatment (with organic or inorganic bases) of the solid materials, solutions or dispersions containing the novel pyrrolopyrroles in organic or aqueous media, polymer solutions or melts. These conversion methods can also be combined, thereby permitting the coloration of paint systems, printing inks, especially for ink jet printing, and plastics, also in fibre form, with unexpectedly enhanced properties such as purity, colour strength, brilliance and transparency, as well as interesting applications in the analytical field.

Accordingly, a further object of the invention is high molecular weight organic material containing in the mass a pyrrolo[3,4-c]pyrrole of formula

which is produced in situ by thermal, photolytic or chemical degradation of a pyrrolo[3,4-c]pyrrole of formula I, in which formula (VIII) above A and B are as defined for formula I, as well as heat-sensitive, photosensitive or chemosensitive recording material and also photo- and electroluminscent materials containing a pyrrolo[3,4-c]pyrrole of formula I.

It has even been found that the chemical treatment of specific pyrrolo[3,4-c]pyrroles of formula I with an organic or inorganic acid at 50° to 150° C. and subsequent cooling to ≦30° C., or the thermal treatment of said compounds by heating to the temperature range from 180°–350° C. can result in new crystal modifications of the corresponding pyrrolo[3,4-c]pyrroles of formula VIII.

The invention therefore additionally relates to a process for the preparation of new crystal modifications of pyrrolo [3,4-c]pyrroles of formula VIII comprising a) the chemical treatment of a pyrrolo[3,4-c]pyrrole of formula I with an organic or inorganic acid at 50° to 150° C. and subsequent cooling to ≦30° C., or b) the thermal treatment of a pyrrolo[3,4-c]pyrrole of formula I in the temperature range from 180° to 350° C.

The invention is illustrated in more detail by the following Examples.

EXAMPLE 1

To a mixture of 14.75 g (0.0512 mol) of 1,4-diketo-3,6-diphenylpyrrolo[3,4-c]pyrrole and 3.23 g (0.0264 mol) of 4-dimethylaminopyridine in 500 ml of tetrahydrofuran (dried over a molecular sieve) are added 27.94 g (0.128 mol) of di-tert-butyldicarbonate in 3 portions over 1 hour. The resultant red suspension is stirred for 2 hours at room temperature with the exclusion of atmospheric moisture. A dark green solution is obtained. The solvent is distilled off under reduced pressure. The yellow residue is washed with a 5% aqueous solution of sodium hydrogencarbonate, rinsed with water and dried under vacuum, affording 24.5 g (98% of theory) of the pyrrolo[3,4-c]pyrrole of formula

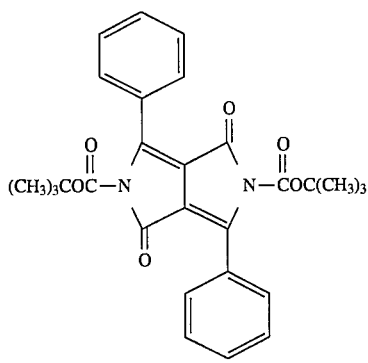

Analysis: $^1$H-NMR (CDCl$_3$): 7.75 (d, 4H); 7.48–7.50 (m, 6H); 1.40 (s, 18H).

EXAMPLE 2

To a suspension of 4.29 g (0.012 mol) of 1,4-diketo-3,6-bis(4-chlorophenyl)pyrrolo[3,4-c]pyrrole in 250 ml of N,N-dimethylformamide (dried over a molecular sieve) are added 0.85 g (0.007 mol) of 4-dimethylaminopyridine followed by 6.55 g (0.030 mol) of di-tert-butyldicarbonate. The reaction mixture is stirred at room temperature with the exclusion of atmospheric moisture. After 2 hours, a further 6.55 g of di-tert-butyldicarbonate are added and stirring is continued for 72 hours. Afterwards, the reaction mixture is poured, with good stirring, into 500 ml of distilled water. The precipitated brown-orange solid is isolated by filtration, the residue is washed with cold distilled water and dried under vacuum at room temperature, affording 6.1 g (91% of theory) of the pyrrolo[3,4-c]pyrrole of formula

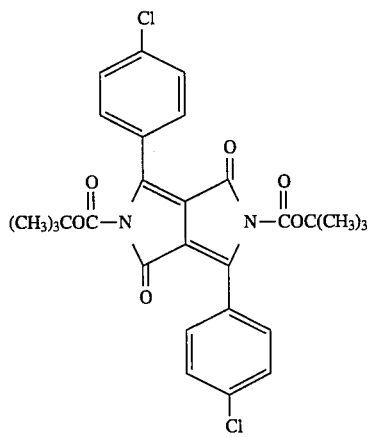

Analysis: $^1$H-NMR (CDCl$_3$): 7.69 (d, 4H); 7.46 (d, 4H); 1.44 (s, 18H).

EXAMPLE 3

To a mixture of 8.44 g (0.021 mol) of 1,4-diketo-3,6-bis(4-tert-butylphenyl)pyrrolo[3,4-c]pyrrole and 1.49 g (0.012 mol) of 4-dimethylaminopyridine in 100 ml of N,N-dimethylformamide (dried over a molecular sieve) are added 24.29 g (0.111 mol) of di-tert-butyldicarbonate. The resultant red suspension is stirred for 3 hours at room temperature, with the exclusion of atmospheric moisture. The colour turns to orange. The precipitated solid is isolated by filtration, and the residue is washed repeatedly with cold distilled water and dried under vacuum at room temperature, affording 11.40 g (90% of theory) of a bright yellow solid of formula

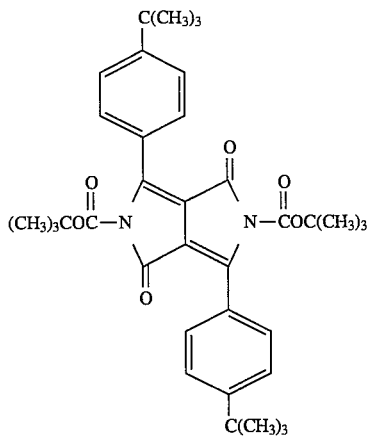

Analysis: $^1$H-NMR (CDCl$_3$): 7.69 (d, 4H); 7.48 (d, 4H); 1.43 (s, 18H); 1.34 (s, 18H).

EXAMPLES 4–12

In accordance with the same general procedure it is possible to obtain from pyrrolo[3,4-c]pyrroles of formula

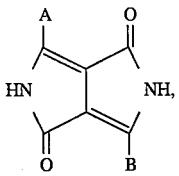

wherein

A and B have the meanings given in columns 2 and 3 of the following Table, the corresponding novel pyrrolo[3,4-c]pyrroles of formula

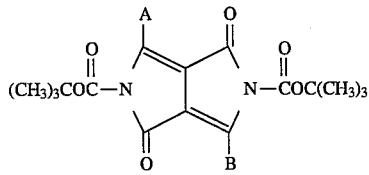

In the following Table, column 4 indicates the solvent, column 5 the reaction time, column 6 the yield and column 7 the data of $^1$H-NMR (CDCl$_3$) analysis.

| Example | A | B | Solvent | Reaction time in h | Yield | $^1$H-NMR(CDCl$_3$) |
|---|---|---|---|---|---|---|
| 4 | -C$_6$H$_4$-CH$_3$ (para) | -C$_6$H$_4$-CH$_3$ (para) | THF | 16 | 94% | 7.65(d, 4H); 7.28(d, 4H); 2, 42(s, 6H); 1, 43(s, 18H) |
| 5 | -C$_6$H$_4$-CH$_3$ (meta) | -C$_6$H$_4$-CH$_3$ (meta) | DMF | 4 | 92% | 7.54–7.57(m, 4H); 7.29–7.39(m, 4H); 2.41(s, 6H); 1.39(s, 18H) |
| 6 | 4-pyridyl | 4-pyridyl | DMF | 20 | 45% | 8.78(d, 4H); 7.56(d, 4H); 1.44(s, 18H) |
| 7 | 3-pyridyl | 3-pyridyl | DMF | 28 | 65% | 8.81(s, 2H); 8.72(d, 2H); 8.19(d, 2H); 7.47(dd, 2H); 1.44(s, 18H) |
| 8 | 3-pyridyl | phenyl | DMF | 20 | 20% | 8.82(d, 2H); 8.51(d, 2H); 8.31(d, 2H); 7.60–7.63(m, 3H); 1.39(s, 18H) |
| 9 | 4-biphenyl | 4-biphenyl | DMF | 28 | 90% | 7.86(d, 4H); 7.72(d, 4H); 7.65(d, 4H); 7.48(t, 4H); 7.40(t, 2H); 1.46(s, 18H) |
| 10 | -C$_6$H$_4$-CN | -C$_6$H$_4$-CN | DMF | 17 | 57% | 7.77–7.84(m, 8H); 1.45(s, 18H); |
| 11 | -C$_6$H$_4$-CH$_3$ (ortho) | -C$_6$H$_4$-CH$_3$ (ortho) | THF | 6 | 28% | 7.42–7.25(m, 8H); 2.48(s, 3H); 2.41(s, 3H); 1.25(s, 18H) |
| 12 | -C$_6$H$_4$-OCH$_3$ (ortho) | -C$_6$H$_4$-OCH$_3$ (ortho) | THF | 6 | 60% | 7.80(d, 2H); 7.45(t, 2H); 7.09(t, 2H); 6.89(d, 2H); 3.90(s, 6H); 1.34(s, 18H) |

THF = tetrahydrofuran
DMF = N,N-dimethylformamide

EXAMPLES 13–16

In general accordance with the procedure described in Example 1, if corresponding dicarbonates are used, the compounds of formula

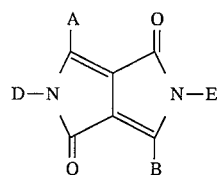

listed in the following Table can be obtained.

| Example | A=B | D=E | Solvent | Reaction time in h | Yield | ¹H-NMR(CDCl₃) |
|---|---|---|---|---|---|---|
| 13 | phenyl | —CO—C(CH₃)(CH₃)—CH₂CH₃ | THF | 24 | 80% | 7.71–7.78(m, 4H); 7.46–7, 52(m, 6H); 1.61–1.71(q, 4H); 1.1(s, 12H); 0.74–0.82(c, 6H) |
| 14 | phenyl | —CO—C(CH₂CH₃)(CH₂CH₃)—CH₂CH₃ | THF | 15 | 30% | 7.71–7.78(m, 4H); 7.42–7.50(m, 6H); 1.78–1.92(q, 12H); .0, 75–0, 90(t, 18H) |
| 15 | phenyl | —CO—C(CH₃)(CH₃)—CH₂—phenyl | THF | 3 | 92% | 7.70–7.78(m, 4H); 7.42–7.51(m, 6H); 7.22–7.38(m, 6H); 7.08–7.12(m, 4H); 2.98(s, 4H); 1.41(s, 12H) |
| 16 | phenyl | —CO—CH(CH₃)(CH₃) | THF | 24 | 36% | 7.68–7.78(m, 4H); 7.46–7.52(m, 6H); 5.00–5.10 (sept., 2H); 1.22(d, 12H). |

EXAMPLE 17

Example 1 is repeated, with the sole exception that di-tert-butyldicarbonate is replaced with an equivalent amount of diethyl dicarbonate, giving the pyrrolo[3,4-c]pyrrole of formula

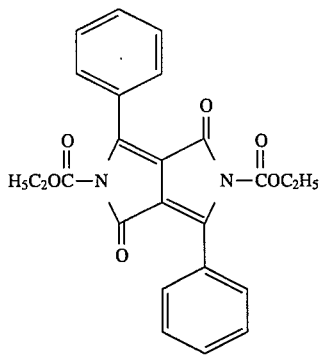

in a yield of 67% of theory.

Analysis: ¹H-NMR (CDCl₃): 7.75 (m, 4H); 7.49 (m, 6H); 4.31 (q, 4H); 1.22 (t, 6H).

EXAMPLE 18

14.93 g of N,N'-bis(tert-butoxycarbonyl)-1,4-diketo-3,6-diphenylpyrrolo[3,4-c]pyrrole, prepared as described in Example 1, are recrystallised from 1.1 liter of boiling ethanol. The precipitated red crystals are chromatographed over a column of silica gel with the solvent system consisting of methylene chloride/ethyl acetate 9:1, affording the diketopyrrolo[3,4-c]pyrrole of formula

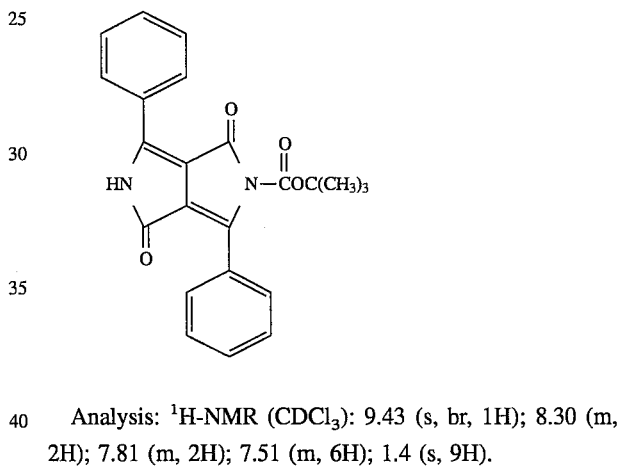

Analysis: ¹H-NMR (CDCl₃): 9.43 (s, br, 1H); 8.30 (m, 2H); 7.81 (m, 2H); 7.51 (m, 6H); 1.4 (s, 9H).

EXAMPLES 19–25

In analogous manner, it is possible to prepare from the corresponding disubstituted pyrrolo[3,4-c]pyrroles the monosubstituted compounds of formula

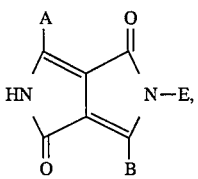

listed in the following Table.

| Example | A | B | E | $^1$H-NMR(CDCl$_3$) |
|---|---|---|---|---|
| 19 | 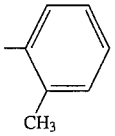 | 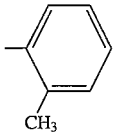 | 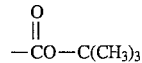 | 7.87(s, br, 1H); 7.80(d, 1H); 7.48–7.23(m, 7H); 2.60(s, 3H); 2.45(s, 3H); 1.22(s, 9H) |
| 20 | 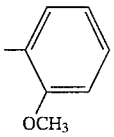 | 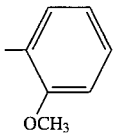 | 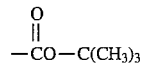 | 9.32(s, br, 1H); 9.24(d, 1H); 7.80(d, 1H); 7.58–7.40(m, 2H); 7.20(t, 1H); 7.11(t, 1H); 7.01(d, 1H); 6.90(d, 1H); 3.99(s, 1H); 3.71(s, 3H); 1.37(s, 9H) |
| 21 | 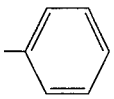 |  | 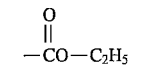 | 9.88(s, br, 1H); 8.34(d, 2H); 7.80(m, 2H); 7.52(m, 6H); 4.35(q, 2H); 1.24(t, 3H) |
| 22 | 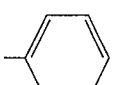 |  | 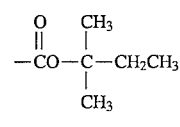 | 9.65(s, br, 1H); 8.31–8.33(m, 2H); 7.81–7.83(m, 2H); 7.50–7.56(m, 6H); 1.70(q, 2H); 1.46(s, 6H); 0.80(t, 3H); |
| 23 | 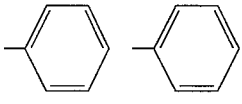 |  | 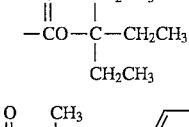 | 9.57(s, br, 1H); 8.26–8.36(m, 2H); 7.78–7.88(m, 2H); 7.48–7.60(m, 6H); 1.82–1.97(q, 6H); 0.78–0.92(t, 9H) |
| 24 | 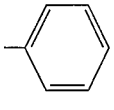 |  | 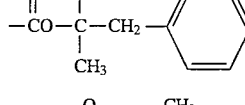 | 8.59(s, br, 1H); 8.20–8.29(m, 2H); 7.72–7.80(m, 2H); 7.42–7.61(m, 6H); 7.24(s, 3H); 7.10–7.16(m, 2H); 3.00(s, 3H); 1.41(s, 6H) |
| 25 | 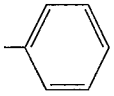 |  | 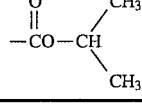 | 9.34(s, br, 1H); 8.25–8.36(m, 2H); 7.75–7.85(m, 2H); 7.48–7.60(m, 6H); 5.03–5.11(sept, 1H); 1.28(d, 6H) |

EXAMPLE 26

To a suspension of 0.5 g (0.00175 mol) of 1,4-diketo-3,6-diphenylpyrrolo[3,4-c]pyrrole in 17 ml of tetrahydrofuran are added, under argon, 0.28 g (0.007 mol) of solid sodium hydride. After stirring for 24 hours, 0.67 ml (0.007 mol) of n-butyl chloroformate are added and the suspension is stirred overnight. The mixture is filtered and the filtrate is concentrated under vacuum. The residue is taken up in water/diethyl ether, the organic phase is dried over MgSO$_4$ and then concentrated under vacuum. The residue is taken up in n-hexane and the precipitated yellow powder is collected by filtration and washed with a minor amount of n-hexane, giving 0.62 g (73% of theory) of N,N'-bis(n-butoxycarbonyl)-1,4-diketo-3,6-diphenylpyrrolo[3,4-c]pyrrole as a yellow fluorescent powder.

Analysis: $^1$H-NMR (CDCl$_3$): 7.72 (m, 4H); 7.49 (m, 6H); 4.32 (q, 4H); 1.23 (t, 6H).

EXAMPLE 27

0.07 g of N,N-bis(tert-butoxycarbonyl)-1,4-diketo-3,6-diphenyl-pyrrolo[3,4-c]pyrrole of Example 1 are heated in a test tube for 10 minutes at 180° C. All analytical data obtained for the resultant red powder are in accord with those of 1,4-diketo-3,6-diphenylpyrrolo[3,4-c]pyrrole. The conversion yield is 99%.

EXAMPLE 28

0.07 g of N,N-bis(tert-butoxycarbonyl)-1,4-diketo-3,6-diphenylpyrrolo[3,4-c]pyrrole of Example 1 are dissolved in 1 ml of acetone and the solution is then added all at once to 1 ml of 33% HCl. All analytical data obtained for the resultant red powder are in accord with those of 1,4-diketo-3,6-diphenylpyrrolo[3,4-c]pyrrole. The conversion yield is 99%.

EXAMPLE 29

A mixture of 1.5 g of the product of Example 2 and 5.1 g of toluene-4-sulfonic acid monohydrate in 75 ml of tetrahydrofuran is stirred for 15 hours under reflux and then cooled to 30° C. The precipitated pigment is isolated by filtration, washed with methanol and then with water and dried, affording 0.55 g (57.2% of theory) of a red powder (β modification of 1,4-diketo-3,6-bis(4-chlorophenyl)-pyrrolo[3,4-c]pyrrole).

| Analysis: | C | H | N | Cl |
|---|---|---|---|---|
| calcd: | 60.53% | 2.82% | 7.84% | 19.85% |
| found: | 60.38% | 2.96% | 7.69% | 19.42% |

The X-ray diffraction pattern is characterised by the following diffraction lines:

| Interplanar spacing (d-Werte in Å) | Two-fold hue angle (2 Θ) | Relative intensity |
|---|---|---|
| 15.2265 | 5.80 | 25 |
| 7.5110 | 11.77 | 27 |
| 6.5395 | 13.53 | 20 |
| 5.9710 | 14.82 | 42 |
| 5.0037 | 17.71 | 11 |
| 4.8711 | 18.20 | 12 |
| 3.8033 | 23.37 | 25 |
| 3.6411 | 24.43 | 14 |
| 3.2721 | 27.23 | 100 |
| 3.0229 | 29.53 | 27 |

The X-ray diffraction pattern of the less yellowish α-modification (starting material of Example 2) is characterised by the following diffraction lines:

| Interplanar spacing (d-values in Å) | Two-fold hue angle (2 Θ) | Relative intensity |
|---|---|---|
| 11.7826 | 7.50 | 22 |
| 5.8252 | 15.20 | 19 |
| 3.6236 | 24.55 | 18 |
| 3.4612 | 25.72 | 41 |
| 3.3081 | 26.93 | 8 |
| 3.1570 | 28.25 | 100 |
| 2.8750 | 31.08 | 32 |
| 2.7828 | 32.08 | 17 |

What is claimed is:

1. A process for the preparation of a pyrrolo[3,4-c]pyrrole of formula

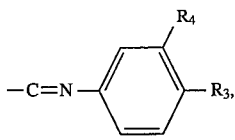

wherein

A and B are each independently of the other a group of formula

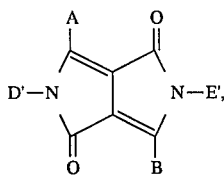

,

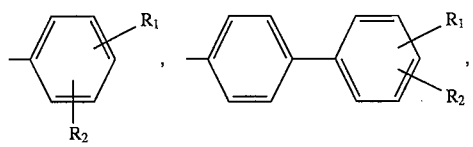

,

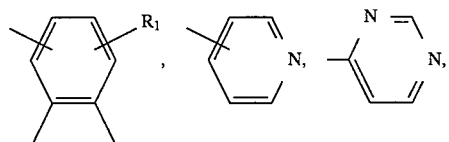

,

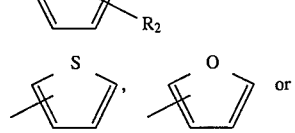

or

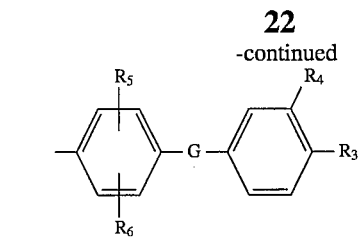

wherein $R_1$ and $R_2$ are each independently of the other hydrogen, halogen, $C_1$–$C_{18}$alkyl, $C_1$–$C_{18}$alkoxy, $C_1$–$C_{18}$alkylmercapto, $C_1$–$C_{18}$alkylamino, —CN, —$NO_2$, -phenyl, trifluoromethyl, $C_5$–$C_6$cycloalkyl, —C≡N—($C_1$–$C_{18}$alkyl), imidazolyl, pyrrazolyl, triazolyl, piperazinyl, pyrrolyl, oxazolyl, benzoxazolyl, benzothiazolyl, benzimidazolyl, morpholinyl, piperidinyl or pyrrolidinyl, G is —$CH_2$—, —CH($CH_3$)—, —C($CH_3$)$_2$—, —CH=N—, —N=N—, —O—, —S—, —SO—, —$SO_2$— or —$NR_7$—, $R_3$ and $R_4$ are each independently of the other hydrogen, halogen, $C_1$–$C_6$alkyl, $C_1$–$C_{18}$alkoxy or —CN, $R_5$ and $R_6$ are each independently of the other hydrogen, halogen or $C_1$–$C_6$alkyl and $R_7$ is hydrogen or $C_1$–$C_6$alkyl, D' and E' are each independently of the other a group of formula

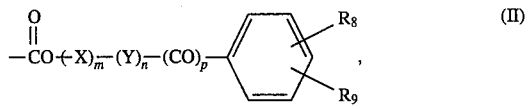 (II)

 (III)

or

 (IV)

and D' may also be hydrogen, and in formulae II, III and IV m, n and p are each independently of one another 0 or 1, X is $C_1$–$C_{14}$alkylene or $C_2$–$C_8$alkenylene, Y is a group —V—($CH_2$)$_q$—, Z is a group —V—($CH_2$)$_r$—, V is $C_3$–$C_6$cycloalkylene, q is an integer from 1 to 6, and r is an integer from 0 to 6, $R_8$ and $R_9$ are each independently of the other hydrogen, $C_1$–$C_6$alkyl, $C_1$–$C_4$alkoxy, halogen, CN, $NO_2$, unsubstituted phenyl or phenoxy or phenyl or phenoxy which are substituted by $C_1$–$C_4$alkyl, $C_1$–$C_4$alkoxy or halogen, Q is hydrogen, CN, Si($R_8$)$_3$, is a group $C(R_{12})(R_{13})(R_{14})$, wherein $R_{12}$, $R_{13}$ and $R_{14}$ are halogen, a group

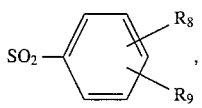

wherein $R_8$ and $R_9$ are as defined above, a group $SO_2R_{15}$ or $SR_{15}$, wherein $R_{15}$ is $C_1$–$C_4$alkyl, a group $CH(R_{16})_2$, wherein $R_{16}$ is unsubstituted phenyl or phenyl which is substituted by $C_1$–$C_4$alkyl, $C_1$–$C_4$alkoxy or halogen, or a group of formula

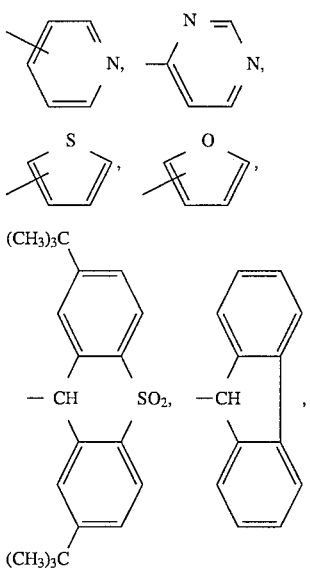

$R_{10}$ and $R_{11}$ are each independently of the other hydrogen, $C_1$–$C_{18}$alkyl a group

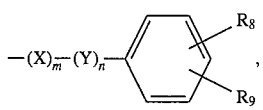

wherein X, Y, $R_8$, $R_9$, m and n are as defined above, or $R_{10}$ and $R_{11}$, together with the linking nitrogen atom, form a pyrrolidinyl, piperidinyl or morpholinyl radical, which process comprises reacting a pyrrolo[3,4-c]pyrrole of formula

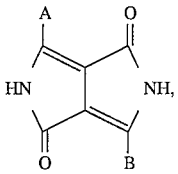

(VIII)

wherein A and B are as defined above, in the desired molar ratio with a dicarbonate of formula

E'-O-E'      (IX)

or with a trihaloacetate of formula $(R_{17})_3$C-E'      (X)

or with a 1:1 mixture of a dicarbonate of formula IX and a dicarbonate of formula

D'-O-D'      (XI)

or with a 1:1 mixture of a trihaloacetate of formula X and a trihaloacetate of formula $(R_{17})_3$C-D'      (XII), or with an azide of formula

E'N$_3$      (XIII), which may also be used in a 1:1 mixture with

D'N$_3$      (XIV)

or with a carbonate of formula

E'-OR$_{18}$      (XV), which may also be used in a 1:1 mixture with

D'-OR$_{18}$      (XVI)

or with an alkylidene-iminooxyformate of formula

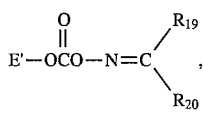

(XVII)

which may also be used in a 1:1 mixture with

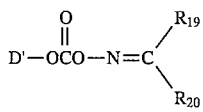

(XVIII)

wherein D' and E' are each as defined above, $R_{17}$ is chloro, fluoro or bromo, $R_{18}$ is $C_1$–$C_4$alkyl or unsubstituted phenyl or phenyl which is substituted by halogen, $C_1$–$C_4$alkyl, $C_1$–$C_4$alkoxy or —CN, $R_{19}$ is —CN or —COOR$_{18}$, and $R_{20}$ is unsubstituted phenyl or phenyl which is substituted by halogen, $C_1$–$C_4$alkyl, $C_1$–$C_4$alkoxy or —CN, in an aprotic organic solvent and in the presence of a base as catalyst, conveniently in the temperature range from 0° to 400° C., preferably from 20° to 200° C., for 2 to 80 hours, to form the pyrrolo[3,4-c]pyrrole of formula (VII);

and then isolating, and optionally purifying, said pyrrolo [3,4c]pyrrole.

2. A process according to claim 1, which comprises reacting the pyrrolo[3,4-c]pyrrole of formula VIII with a dicarbonate of formula IX or with a 1:1 mixture of a dicarbonate of formula IX and a dicarbonate of formula XI.

3. A process according to claim 1, wherein the pyrrolo[3, 4-c]pyrrole of formula (VII) is prepared wherein A and B are each independently of the other a group of formula

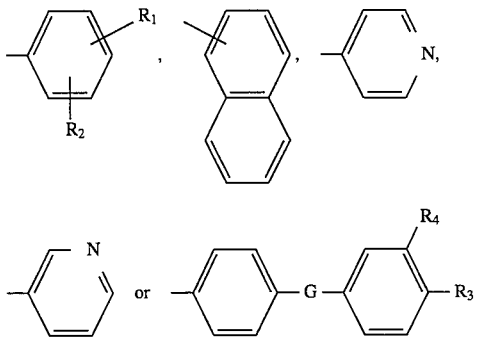

wherein $R_1$ and $R_2$ are each independently of the other hydrogen, chloro, bromo, $C_1$–$C_4$alkyl, $C_1$–$C_6$alkoxy, $C_1$–$C_6$alkylamino, CN or phenyl, G —O—, —NR$_7$—, —N=N— or —SO$_2$—, $R_3$ and $R_4$ are hydrogen and $R_7$ is hydrogen, methyl or ethyl.

4. A process according to claim 1, wherein the pyrrolo[3, 4-c]pyrrole of formula (VII) is prepared wherein A and B are both identical.

5. A process according to claim 1, wherein the pyrrolo[3, 4-c]pyrrole of formula (VII) is prepared wherein A and B are a group of formula

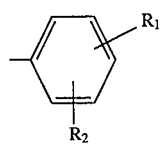

wherein $R_1$ and $R_2$ are each independently of the other hydrogen, methyl, tert-butyl, chloro, bromo, CN or phenyl.

6. A process according to claim 1, wherein the pyrrolo[3, 4-c]pyrrole of formula (VII) is prepared wherein D' is hydrogen or has the meaning of E' and E' is a group of formula

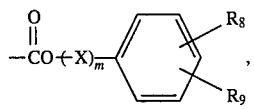   (V)

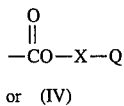   (VI)

or   (IV)

wherein m is 0 or 1,

X is $C_1$–$C_4$alkylene or $C_2$–$C_5$alkenylene, $R_8$ and $R_9$ are each independently of the other hydrogen, $C_1$–$C_4$alkyl, methoxy, chloro or —NO$_2$—, and Q is hydrogen, CN, CCl$_3$, a group

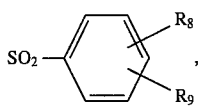

SO$_2$CH$_3$ or SCH$_3$, $R_{10}$ and $R_{11}$ are each independently of the other hydrogen, $C_1$–$C_4$alkyl or a group

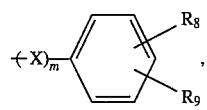

or $R_{10}$ and $R_{11}$, taken together, form a piperidinyl radical, with the proviso that, if D' and/or E' is a group of formula IX and Q is hydrogen, X must be a group

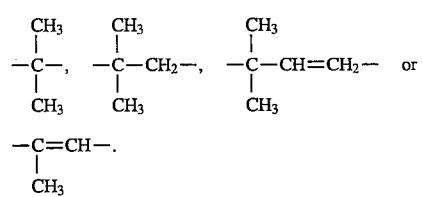

7. A process according to claim 1, wherein the pyrrolo[3, 4-c]pyrrole of formula (VII) is prepared wherein D' and E' are identical and are a group of formula

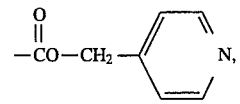

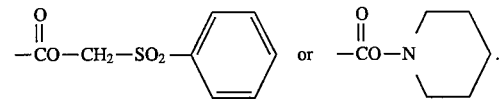

* * * * *